Figure 1:
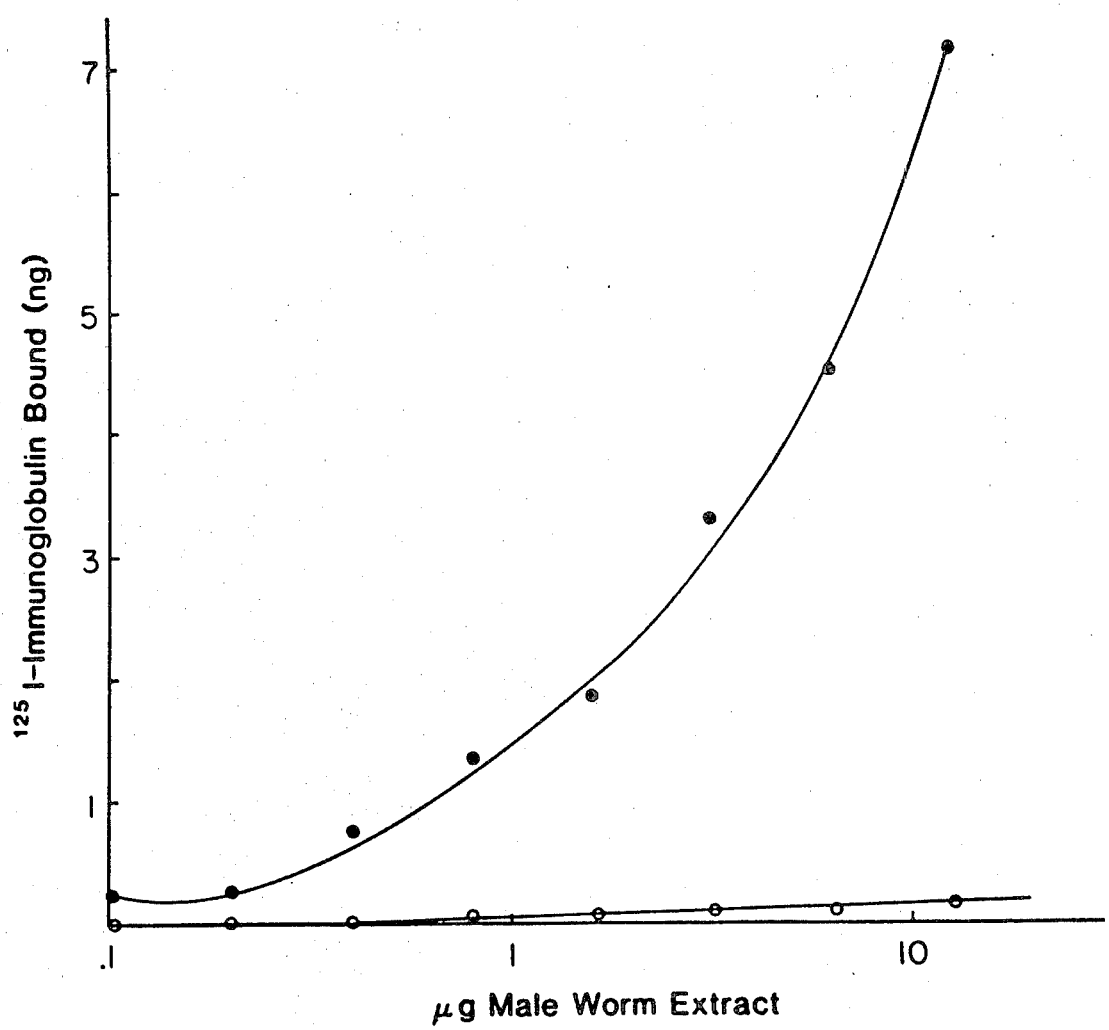

United States Patent [19]

Strand

[11] 4,416,866

[45] Nov. 22, 1983

[54] DIAGNOSIS AND TREATMENT OF FLUKE INFECTIONS WITH MONOCLONAL ANTIBODIES

[75] Inventor: Mette Strand, Baltimore, Md.

[73] Assignee: The Johns Hopkins University, Baltimore, Md.

[21] Appl. No.: 297,290

[22] Filed: Aug. 28, 1981

[51] Int. Cl.³ .................................. G01N 33/00
[52] U.S. Cl. .............................. 424/1.1; 436/548; 436/536; 424/9
[58] Field of Search ................... 424/1, 1.5, 12, 9; 435/7, 172; 436/536, 548

[56] References Cited

PUBLICATIONS

*Biological Abstracts*, vol. 70(II), p. 7495, Abstract 71676, Verwaerde et al., (1980).
*Proc. National Acad. Sci. USA*, vol. 78(5), pp. 3165–3169, (1981), Mitchell et al.
*Aust. J. Exp. Biol. Med. Sci.*, vol. 57, pp. 287–302 (1979), Mitchell et al.
*C. R. Acad. Sc. Paris*, t. 289 (Oct. 29, 1979), Serie D—725 (Translation Provided).

*Primary Examiner*—Benjamin R. Padgett
*Assistant Examiner*—M. Moskowitz
*Attorney, Agent, or Firm*—Schuyler, Banner, Birch, McKie & Beckett

[57] ABSTRACT

Antibodies and antigens are disclosed which provide a method of detecting and a method of combating flukes. Fluke infections are screened by determining presence of fluke antigens defined by antibodies produced by hybridomas ATCC HB-8086 and HB-8087. Chronic and acute fluke infections are distinguished by determining presence of fluke spine protein. Fluke infections are combated by injecting warm-blooded animals with antibodies produced by hybridomas ATCC HB-8086, HB-8087 and HB-8088, or with proteins defined by those antibodies.

9 Claims, 4 Drawing Figures

BINDING OF ¹²⁵I-LABELED ANTIBODY TO VARYING ANTIGEN CONCENTRATIONS

OPEN SYMBOLS = 200 ng OF CONTROL IMMUNOGLOBULIN.
CLOSED SYMBOLS = 200 ng TEST IMMUNOGLOBULIN.

*THE CONCENTRATIONS OF MALE WORM PROTEIN EXTRACT ARE INDICATED.*

BINDING OF $^{125}$I-LABELED ANTIBODY TO VARYING ANTIGEN CONCENTRATIONS

OPEN SYMBOLS = 200 ng OF CONTROL IMMUNOGLOBULIN.
CLOSED SYMBOLS = 200 ng TEST IMMUNOGLOBULIN.

*THE CONCENTRATIONS OF MALE WORM PROTEIN EXTRACT ARE INDICATED.*

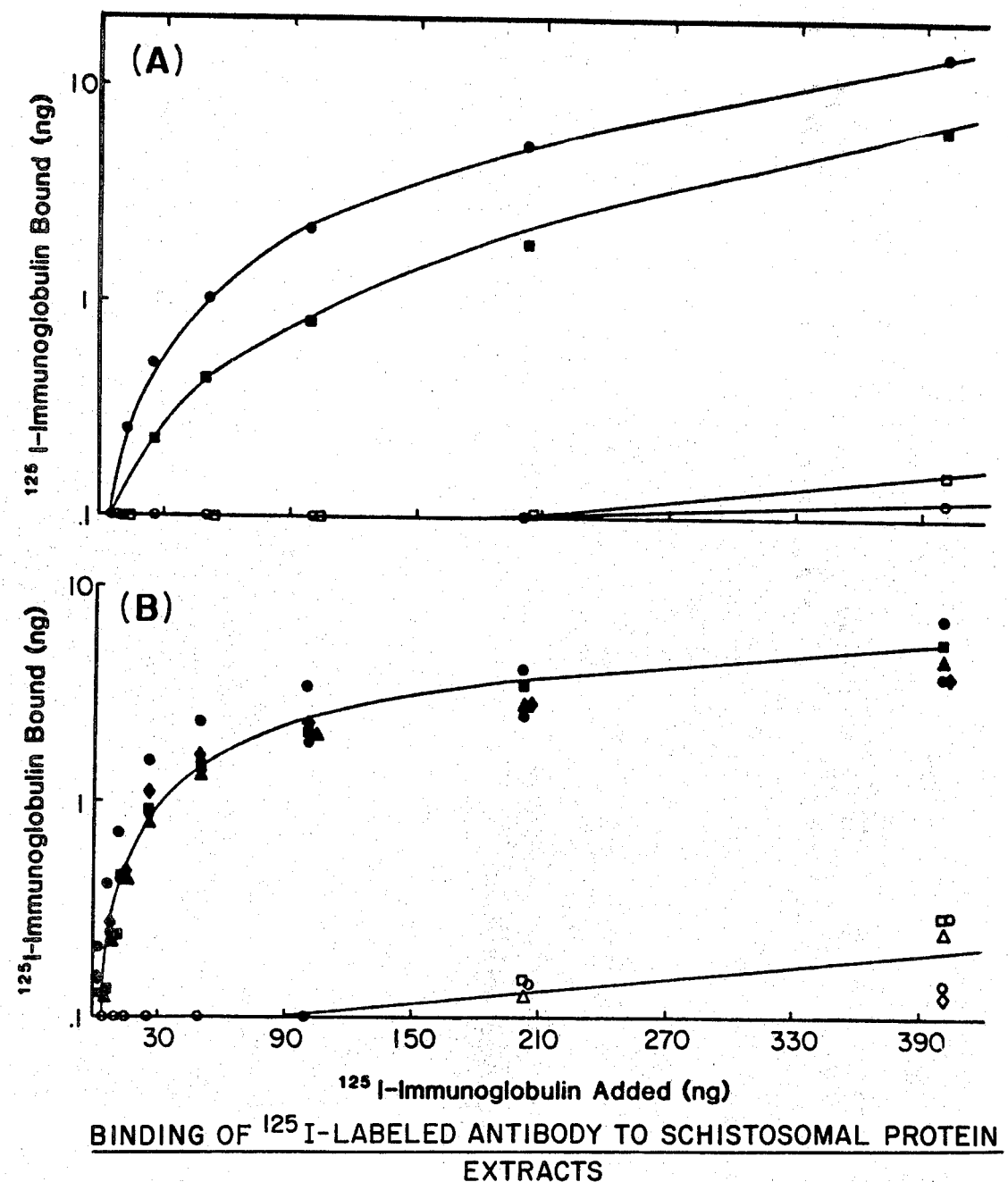

BINDING OF $^{125}$I-LABELED ANTIBODY TO SCHISTOSOMAL PROTEIN EXTRACTS (A) – OPEN SYMBOLS = CONTROL IMMUNOGLOBULIN.
CLOSED SYMBOLS = TEST IMMUNOGLOBULIN.
5 μg EACH OF MALE (o) OR FEMALE (□) WORM PROTEIN EXTRACT.

(B) – OPEN SYMBOLS = CONTROL IMMUNOGLOBULIN P3x63Ag8;
CLOSED SYMBOLS = TEST IMMUNOGLOBULIN.
5μg EACH OF PROTEIN EXTRACTS: CERCARIAL 27K SUPER-
NATANT (o), CERCARIAL 3XF+T (□), CERCARIAL TRITON 305 (Δ),
CERCARIAL LYSIS EXTRACT (o), EGG EXTRACT (◊).

FIG. 2

BINDING OF $^{125}$I-LABELED ANTIBODY TO VARYING CONCENTRATIONS OF MALE WORM PROTEIN EXTRACT.

BINDING OF $^{125}$I-LABELED ANTIBODY TO SCHISTOSOMAL PROTEIN EXTRACTS

THE CURVES REPRESENT 25 µg EACH OF CERCARIAL TRITON X-305 PROTEIN EXTRACT (△), MALE WORM PROTEIN EXTRACT (○), FEMALE WORM PROTEIN EXTRACT (□), AND EGG PROTEIN EXTRACT (▽).

DIAGNOSIS AND TREATMENT OF FLUKE INFECTIONS WITH MONOCLONAL ANTIBODIES

Flukes, trematodes, are responsible for widespread and severe disease in infected humans. These parasites pass through several stages of growth but in the mature state in the definitive host are present as worms. The parasites can cause a variety of detrimental effects and can, at times be fatal to the host.

The genus Schistosoma, for example, embraces flukes which have a significant medical impact. Schistosomiasis, known as bilharziasis in Europe and as big belly disease in China, ranks as one of the most widespread and debilitating of tropical infections. Schistosomiasis is the pathological consequence of infection with sexually mature and reproducing adult worms of any one of several closely related species of digenetic trematodes. Schistosomes differ from all other digeneans in that the sexes are separate.

Schistosomes lead a complex life. Part of their life cycle must occur within a water dwelling snail. The mobile larvae (cercariae) that emerge from the snail penetrate the intact skin of the definitive host (e.g., man or animals). Upon penetration, the cercariae shed their tails and rapidly evolves in a matter of minutes into schistosomula. The schistosmula migrate to the lungs and are retained there for several days. Thereafter, the schistosomula migrate into the vascular system and to the mesenteric veins, where they sexually mature into inch long male or female worms. They can live for up to 25 years paired in perpetual copulation producing eggs. A pair of worms can produce from 20 to 2000 eggs per day depending on the species. The eggs lodge in various tissues provoking an intense inflammatory response and causing enlargement of the liver and spleen.

Previously, a variety of studies of schistosomiasis have shown that the worm-infected host contains circulating schistosome antigens antibodies and antigen/antibody complexes. The immunopathological basis of schistosomal disease has been appreciated for some time, but progress has been hampered due to the lack of indentification of biologically relevant antigens as well as by difficulties inherent in purification of individual antigens from an organism whose propagation depends upon passage in a mammalian host.

The protein composition of different development stages of *Schistosoma mansoni* has been studied by staining of protein bands after SDS-polyacrylamide slab gel electrophoresis. Despite the differences in the morphology of the developmental stages, their protein composition was similar except for a few distinct sex and stage specific differences. The radiolabeled surface proteins of cercariae and schistosomula also showed similarity. Studies of the schistosomal proteins, carried out chiefly with extracts of adult worms, eggs or circulating antigens, have indicated that several proteins are immunoreactive in the infected host. A few of these proteins have been purified and characterized, but progress has been limited by the small amount of protein which can be obtained from worms and eggs present in the infected animal.

The diagnostic tests presently in use for flukes employ crude antigens and test for the presence of antibodies in serum. Such tests provide undesirable variability due to the nature of the antigen used and often do not differentiate between chronic and acute infection or between past and current infection. Use of any existing test in an effort to differentiate between chronic and acute infections often provides ambiguous results. Indeed, the World Health Organ., Vol. 51, (1974) at page 558 stated:

Immunodiagnostic techniques currently available for routine use lack the accuracy, sensitivity, and specificity characteristic of parasitological methods.

Because of the widespread impact of flukes, there is today a critical need for a reliable and rapid diagnosis and immunoprophylaxis.

One object of this invention is to provide a diagnostic method to identify the presence of flukes.

Another object of this invention is to provide a diagnostic method to differentiate between acute and chronic infection by flukes.

Still another object of this invention is to provide a method of preventing fluke infection.

The present invention arises from several interrelated discoveries regarding flukes. One of the aspects of the invention is premised on the discovery that the membrane of flukes in all growth phases, including eggs, contain two major glycoprotein molecules. One of those molecules is a glycoprotein which is recognized by antibodies produced by fused cell hybrid ATCC HB-8086 (American Type Culture Collection, 12301 Parklawn Drive, Rockville, Md. 20852), while the other molecule is a glycoprotein recognized by antibodies produced by fused cell hybrid ATCC HB-8087. This discovery provides the basis for a reliable screening test. Body fluid or feces can be checked for the existence of these molecules. Indeed, urine or feces readily may be checked for the existence of these glycoproteins and thereby avoid the necessity of drawing blood from the patient.

It has also been discovered that the spine protein of flukes bears antigenic sites which are not shared by the egg of the fluke. Since flukes in all their growth stages, other than the egg, have spines, this discovery provides a facile method of differentiating between current and past infections. Past parasite infections leave a significant residue of inactive or dead eggs (granuloma) in the definitive hose for a long period of time. Since the protein molecule of the spine does not appear in the egg, a test for the spine protein in serum readily eliminates the significant problem of false positives due to residual eggs in the host.

These discoveries can be used in combination to differentiate between acute and chronic infections. Such technique involves a comparison of the antibody response to glycoprotein recognized by fused cell hybrids ATCC HB-8086 or ATCC HB-8087 with the antibody response against the spines. Patients with an acute infection will have a higher ratio of response as compared to those with a chronic infection.

In one aspect of this invention there is provided a diagnostic screening method for the determination of a fluke infection of a warm-blooded animal which comprises testing a body component selected from the group consisting of serum, urine, milk and feces for the presence of glycoprotein molecules identified by antibodies produced by fused cell hybrid ATCC HB-8087 or fused cell hybrid ATCC HB-8086. In yet another embodiment of this invention there is provided a screening test for the determination of an infection of flukes which comprises testing body serum for the presence of antibodies which bind to glycoprotein molecules that are identified by the antibodies produced by fused cell hybrid ATCC HB-8087 or fused cell hybrid ATCC HB-8086.

In accordance with still another embodiment of this invention, there is provided a diagnostic method for the determination of an active fluke infection in a warm-blooded animal which comprises testing body serum for the presence of anti-spine antibodies. In still another embodiment of this invention, there is provided a diagnostic method for the determination of an active infection of flukes which comprises testing body fluids for the presence of fluke spines.

And yet another aspect of this invention, there is provided a diagnostic method for acute infection of flukes which comprises comparing the antibody response to glycoprotein molecules that are identified by the antibodies produced by fused cell hybrid ATCC HB-8087 and ATCC HB-8086 with the antibody response to spines.

In addition, the invention contemplates using the above antibodies and antigens for prevention of infection.

The flukes which can be detected following the practice of this invention are all those within the class Trematoda which include parasites of the genera, Schistosoma, Gastrodiscoides, Watsonius, Fasciola, Fasciolopsis, Chlonorchis, Opisthorchis, Heterophyes, Metagonimus and Paragonimus. Parasites of the genera Schistosoma and Fasciola are particularly insidious and widespread and therefore constituted preferred targets for the practice of this invention. The genera Schistosoma includes the species S. haemotobium, S. mansoni, S. japonicum and S. intercalatum, while the genera Fasciola includes the species F. hepatica and F. gigantica. All are within the scope of this invention.

The hosts to which this invention is directed include warm-blooded animals generally. Such group embraces humans, birds and domestic animals, including, for example, cattle and sheep.

The invention contemplates the use of any test procedure known in the art for the identification of protein molecules. Such measurement can be accomplished utilizing antibody binding quantitated, for example, by an enzyme assay, immunofluorescence, or radioimmunoassay. Other tests known, however, can also be used. Such tests include physical as well as chemical analyses.

Similarly, the invention contemplates the use of any test procedure known in the art to determine the presence of bound antibodies in fluids. Such tests include, inter alia, utilization of plastic surfaces such as polyvinyl chloride and polystyrene on which an antigen is coated. The presence of antibodies is then quantitated by thereafter contacting the antibody with an anti-host immunoglobulin appropriately tagged with, for example, fluorescein, radio labels or enzymes.

In those aspects of this invention which employ a test for antispine antibodies, the spine of any fluke can be used as a basis for a general screening. If desired, however, spines of genera or species can be employed to screen parasites of that genus or species and, of course, spines from more than one parasite can be combined and utilized in a single test. Similarly, glycoprotein from any genus or species which is identified by the antibodies produced by fused cell hybrid ATCC HB-8086 or ATCC HB-8087 can be used.

When employed to combat infection the antibodies or antigens of this invention can be injected in any pharmaceutical carrier including, for example, saline. The amounts to be employed and the protocol for treatment are matters within the skill of the art.

As used herein the term "corresponding to" antibodies produced by the identified fused cell hybrids refers to antibodies which block the attachment of the fused cell hybrid antibody to the protein. Tests to determine blocking are known in the art.

The invention will be better understood from the following detailed discussion.

In the drawings:

FIGS. 1-4 depict assay results obtained in Examples 4 and 5.

The following procedures were employed in the Examples described below.

Schistosomal proteins. Cercariae of the strain Schistosoma mansoni were obtained from Biomphalaria glabrata. Phenylmethylsulfonylfluoride (PMSF) to 2 mM was added to the cercariae immediately after harvesting. Worms and eggs were obtained from mice (strain CD-1, Charles River) infected 8 to 10 weeks previously with 80 cercariae of Schistosoma mansoni by tail immersion (Oliver and Stirewalt 1952).

Human Test sera.

Human sera was obtained from 6 patients living in Northern Egypt in an area endemic for Schistosoma mansoni. The patients showed no signs of infection with Schistosoma hematobium by analysis of their urine and no evidence of heptasoplenic schistosomiasis. Fecal examination for eggs was done by the Kato-technique (Japanese J. of Parasitology, 3, 35–41 (1954)). Patient No. 18, a 15 year old female showed 220 eggs per gram; No. 25, a 25 year old female, 20 eggs per gram; No. 33, an 11 year old male, 200 eggs per gram; No. 42, a 17 year old male, 2,000 eggs per gram; No. 53, a 12 year old female, 400 eggs per gram; and No. 54, a 12 year old male, 2,370 eggs per gram. No. 3496 was a human serum known to be Schistosoma mansoni positive. Control sera were obtained from normal young adults who were not infected.

Purification of Cercarial Glycoproteins

Pellets of cercariae, approximately $8 \times 10^5$ cercariae per ml, were suspended in 50 mM sodium phosphate buffer, pH 7.5, containing 2 mM PMSF and 200 units of Trasylol per ml of extract. The suspension was centrifuged at 27,000×g for 20 min. and both the particulate (27 K pellet) and the supernatant (27 K supernatant) were collected. Membranous components in this supernatant fraction were solubilized by adding KCl to 400 mM and Triton X-100 to 1 percent. Following 3 cycles of freezing and thawing, the suspension was centrifuged at 100,000×g for 60 min. Glycoproteins containing mannose were purified by affinity chromatography on con A-Sepharose (Pharmacia). The 27 K solubilized cercarial protein extract was dialyzed against con A-column buffer (20 mM Tris, pH 7.6, 100 mM NaCl, 0.2 percent Trixon X-100 and 1 mM each of $CaCl_2$, $MgCl_2$ and $MnCl_2$) and applied to a con A-column (2 ml per 10 mg protein) previously equilibrated with the same buffer. In order to prevent leaching of the lectin, the con A-Sepharose was cross-linked prior to use by treatment with 0.25 percent glutaraldehyde for 1 min. at 25° C. (and 60 min. at 0° C. while stirring in 1 M phosphate buffer at pH 7.0 (21). Following the flow through of unadsorbed proteins, the column was eluted with 100 mM α-methyl-D-mannoside in con A-buffer, now containing 1 M NaCl.

Solubilization of Schistosomal Proteins

The solubilization method for cercarial proteins described above yielded about 35 mg (38 percent) of the proteins in the 27 K supernatant. To enhance the yield the 27 K pellet was subjected to osmotic shock treatment by suspension in 50 mM sodium-phosphate buffer, pH 7.5, 25 percent glycerol, 2 mM PMFS, and 200 units of Trasylol per ml. The suspension was frozen and thawed three times, then centrifuged at 27,000×g for 20 min. This procedure solubilized an additional 20 mg (21 percent) of the original cercarial proteins into the supernatant (freeze/thaw fraction). The freeze/thaw pellet was suspended in a buffer containing (20 mM Tris-HCl, pH 7.6, 1 percent Triton X-305, 2 mM PMFS, and 200 units of Trasylol per ml. The suspension was sonified, frozen and thawed three times, then centrifuged at 100,000×g for 60 min. This solubilization procedure yielded an additional 6 mg (6 percent) of the original cercarial proteins into this supernatant (Triton X-305 fraction). The Triton X-305 pellet was finally suspended in lysis-buffer (5 mM Tris-HCl, pH 9.2, 400 mM KCl, 1 percent Triton X-100, 2 mM PMFS, and 200 units of Trasylol per ml). Following sonic treatment and centrifugation as above, the supernatant fluid contained 19 mg (20 percent) of the original cercarial proteins. The combination of solubilization procedures released approximately 85 percent of the total cercarial proteins.

Worm proteins were prepared from adult male or female worms. Worm pairs were harvested from mice infected 8 weeks prior with cercariae and suspended in a large volume of Hank's basic salt solution (HBSS) containing 40 mg dextrose per 100 ml. The worm pairs were chilled on ice for two to four minutes to allow separation of males and females. Pellets of separated male worms or female worms were suspended in lysis buffer (described above). Following sonic treatment and three cycles of freezing and thawing, the suspension was centrifuged at 100,000×g for 60 min. The supernatant fluids were saved and the pellets were discarded. Isolation of male and female glycoproteins was carried out by con A lectin affinity chromatography as described for cercarial glycoproteins.

Eggs were obtained from the livers of infected mice using a modification of the method of Seed and Bennett, Exp. Parasitology, 49, 430–441 (1980). The livers, suspended in a four-fold volume of cold 1.1 percent NaCl, were homogenized in a Waring blender. Trypsin (Sigma type II) was added to a final concentration of 25 units per ml. The homogenate was incubated for one hour at room temperature, then passed sequentially through a series of wire sieves of 40, 60, 140, 170 and 325 mesh. The eggs were washed through each sieve with excess cold 1.1 percent NaCl. The eggs were washed through the 170 mesh sieve onto the 325 mesh sieve two additional times. The extent of purification was monitored microscopically. Pellets of eggs were solubilized exactly as described above for worm protein extract.

Proteins were determined by the method of Schnaffner and Weisman (1973).

Immunization

Two 8 week old C57BL/6 mice were immunized intraperitoneally with 70 μg purified cercariae glycoproteins per injection. The mice received primary immunization of glycoproteins emulsified with equal volumes of Freund's complete adjuvant and six additional immunizations of cercarial glycoproteins in Freund's incomplete adjuvant at two week intervals. The seventh and final injection of glycoprotein in Dulbecco's phosphate-buffered saline (PBS) was given intravenously 3 days prior to fusion.

Cells

The myeloma cell lines (X63-Ag8-653) (Kearney et al., J. Immunology, 123, 1548–1550 (1979)), and P3-X63-Ag8 (Kohler et al., Eur. J. Immunology, 6, 292–295 (1976)), were propagated without antibiotics in Dulbecco's modification of Eagle medium (DME medium) supplemented with 10 percent heat-inactivated fetal calf serum and 20 μg of 8-azaguanine per ml.

Cell Fusion, Cloning, and In Vivo Propagation

Spleen cells ($1 \times 10^8$) were hybridized with X63-Ag8-653 myeloma cells ($2 \times 10^7$) using polyethylene glycol and dimethylsulfoxide according to procedures described in Strand, Nat. Acad. Sci. U.S.A., 77, 3234–3238 (1980). Culture supernatant fluids were assayed for antibody activity by indirect radioimmunoassay; cloning of selected cultures were performed in soft agar. Selected clones were expanded in vivo to obtain antibody-containing ascites fluid by injecting $2 \times 10^7$ hybridoma cells intraperitoneally into (BALB/c×C57BL/6)F$_1$ mice that had been primed with Pristane.

Monoclonal Antibody Binding Assay

Antibody production by hybridomas was measured by solid phase radioimmunoassay in polystyrene microtiter wells (Falcon, Oxnard, CA). Briefly, microtiter wells were incubated at 37° C. for 15 min. with 50 μl per well of a 0.25 mg/ml solution of poly-L-lysine in PBS with 0.02 percent NaN$_3$. After washing with the same buffer, 50 μl containing 5 μg of protein extract in Dulbecco's phosphate buffered saline without CaCl$_2$ and MgCl$_2$ (PBS) with 0.02 percent NaN$_3$ were added to each well, followed by incubation overnight at 37° C. The remaining protein-binding sites in the well were then saturated by the addition of 200 μl of PBS containing 5 percent calf serum, 0.1 percent Triton X-100 and 0.02 percent NaN$_3$, and the wells incubated for an additional 90 min at 37° C. After removal of this buffer, 50 μl of culture supernatants containing monoclonal antibodies were added and the wells incubated for 1 hour at 37° C. After three washings with the above buffer, bound antibodies were quantitated by addition of $^{125}$I-labeled goat IgG directed against mouse Ig (Strand, Nat'l. Acad. Sci. U.S.A., 77, 3234–3238, (1980)). Unbound antibody was again removed by washing. After incubation with 80 μl of 2 M NaOH for 15 min. at 65° C., the solubilized proteins were transferred to glass tubes and the radioactivity was measured in an LKB gamma counter.

Determination of Monoclonal Antibody Immunoglobulin Class

Immunoglobulin class of the monoclonal antibodies was determined by use of the solid phase radioimmunoassay described above with the following modifications. Ig class-specific antisera (goat IgG anti-mouse, u, $\gamma_1$, $\gamma_{2a}$, $\gamma_{2b}$, $\gamma_3$, and A) (Litton Bionetics, MD) were added to the bound washed hybridoma antibodies (instead of $^{125}$I-labeled goat IgG anti-mouse Ig), and incubated for 1 hour at 37° C. After three washings $^{125}$I-labeled pig IgG directed against goat IgG was then added and the assay was processed as described.

Direct Binding Assay of Monoclonal Antibody

Binding of $^{125}$I-labeled monoclonal antibodies to schistosomal proteins was measured as described above.

Iodination

The schistosomal proteins were iodinated by the chloramine-T method (Hunter, Handbook of Exp. Immunology, F. A. Davis Co., p. 608–642, (1967)) except the reaction was terminated by excess cold tyrosine as described in Jensenius and Williams, Eur. J. Immunol., 4, 91–97, (1974). Specific activity was 10 to 50 μCi per ug. All the immunoglobulins (goat IgG anti-mouse Ig, pig IgG, anti-goat IgG, and monoclonal antibodies were iodinated as here described. Specific activity was 10 to 25 μCi per ug.

Immunoprecipitation, Gel Electrophoresis, and Autoradiography $^{125}$I-labeled proteins (1 to $2\times10^6$ cpm) were incubated for 10 hours at 0° C. with 1 μl of human sera, 4 μl of mouse sera or 2 ul of ascites fluid in a total volume of 200 ul containing 20 mM Tris-HCl, pH 8.2, 150 mM NaCl, 0.2 percent Triton X-100 and 2 mM PMFS. All reactions were carried out in siliconized glass tubes. The immunocomplexes were precipitated with 80 μl of 10 percent *Staphylococcus aureus* (strain Cowan) prepared as described by Kessler (1975). The immunoprecipitates were washed with 1.5 ml of cold TEN buffer (20 mM Tris-HCl, pH 8.2, 1 mM ethylenediaminetetraacetate (EDTA), 100 mM NaCl) containing 0.5 percent NP40 and 2.5 M KCl (Jay et al. 1978) and were collected by centrifugation at $1700\times g$ for 15 min. The washing were repeated and the precipitates were suspended in 1 ml of 20 mM Tris-HCl, pH 8.2 and transferred into fresh tubes. Following centrifugation the precipitates were suspended in electrophoresis sample buffer (62.5 mM Tris-HCl, pH 6.8, 2 percent (wt/vol) sodium dodecyl sulfate (SDS), 5 percent (vol/vol) 2-mercaptoethanol, 10 percent (vol/vol) glycerol/2 mM EDTA, 8 M urea). The solubilized precipitates were boiled for 2 min. and the bacterial adsorbant was removed by centrifugation. These supernatants were analyzed by electrophoresis in a high-resolution, 5–20 percent (wt/vol) gradient polyacrylamide gel in the presence of 0.1 percent (wt/vol) SDS, as described by Baum et al., J. Virology, 10, 211–219 (1972). $^{125}$I-labeled proteins in the gels were detected by autoradiography using Kodak NS-5 film or Kodak X-Omat XR-5 film in the presence of an intensifying screen (Swanstrom and Shank, Analytical Biochem., 86, 184–192 (1978)). Two dimensional gel electrophoresis was conducted essentially as described by O'Farrell, J. Biol. Chem., 250, 4007–4021 (1974). In this case the immunoprecipitates were suspended in O'Farrell's lysis buffer and incubated for 4 hours at 37° C. The solubilized proteins were applied to the isoelectric focusing gels.

Purification of Monoclonal Antibody

Class IgA immunoglobulins of the hybridoma clone were purified from ascites fluid. The antibodies were precipitated with ammonium sulfate at a final concentration of 50 percent saturation, dialyzed against 20 mM sodium phosphate, (pH 7.4) containing 150 mM NaCl and applied to an Affi-gel Blue column (Bio-Rad) (5 ml resin per ml ascites) equilibrated with the same buffer. The IgA was eluted by applying a gradient of 0.15 M to 1.5 M NaCl in 20 mM sodium phosphate, pH 7.4 to the column. The extent of purification was assessed by SDS polyacrylamide gel electrophoresis. The fractions which contained only IgA were pooled and concentrated using vacuum dialysis (miro-ProDiCon). Monoclonal IgG$_1$ was purified from ascites fluid by affinity chromatography on protein A-sepharose (Pharmacia) as described by Ey et al., Immunochemistry, 15, 429–436 (1978).

Two-Dimensional Tryptic Peptide Analysis

Glycoproteins labeled with $^{125}$Iodine were isolated by immunoprecipitation and SDS-gel electrophoresis. The labeled proteins were localized by radioautography and exised from the gel. Proteolytic peptide digestion was carried out as described by Van de Ven et al., J. Virology, 35, 165–175 (1980). Gel slices were washed with 50 mM NH$_4$HCO$_3$ buffer, and suspended in 0.5 ml of the same buffer containing 12.5 ug tosylamide phenylethyl chloromethyl ketone-trypsin (TPCK-trypsin) (Worthington Biochemical Corporation, N.J.). The gel slices were triturated with a glass rod and incubated at room temperature overnight. Supernatant fluids were removed and replaced with a fresh TPCK-trypsin solution for additional digestion at 37° C. for 6 hours. The supernatant fractions were pooled, filtered and evaporated to dryness in vacuo. The peptide products were washed with 0.5 ml of deionized water, again evaporated to dryness and analyzed by electrophoresis and ascending chromatography on cellulose plates as previously described (Krantz et al., J. Virology, 22, 804–815 (1977)).

Indirect Immunofluorescence

Approximately 1500 fixed or unfixed schistosomula were suspended in 0.5 ml of PBS. Heat-inactivated serum, hybridoma ascites fluid, or purified immunoglobulin was added and the suspensions were incubated with gentle agitation for b 30 min. at 37° C. The schistosomula were washed twice with 10 ml of PBS to remove unbound immunoglobulins, and then suspended in 0.5 ml of PBS. Fluoresceinated goat anti-murine-IgG (prepared by Huntingdon Research and obtained from the Division of Cancer Cause and Prevention, National Cancer Institute) was added and the suspension incubated with gentle agitation for 30 min. at 37° C. Stained organisms were mounted under coverslips on glass slides in 50 percent glycerol in PBS, and examined immediately in a Zeiss Universal microscope equipped for incident light immunofluorescence with mercury vapor and xenon lamps. Photographic exposures were made on Kodak Tri-X-Pan film at ASA 400/27 DIN, using a Zeiss MC-63 automatic exposure meter.

Direct Immunofluorescence

Immunoglobulins were conjugated with tetramethylrhodamine isothiocyanate (RITC; Baltimore Biological Laboratories) as described by Preud'homme and Labaume, Ann. N.Y. Academy of Sci., 254–261 (1975). Briefly, the immunoglobulins were dialyzed overnight against 200 mM NaCl, 50 mM bicarbonate buffer, pH 9.5, containing 100 μg/ml RITC. After extensive dialysis against PBS, the labeled antibodies were diluted in PBS containing 1.5 mg/ml bovine serum albumin (BSA) and separated from free rhodamine on a 0.7 cm×8 cm Sephadex G-25 column.

Artificially transformed schistosomula and worms obtained from infected mice as described above were fixed for 5 minutes in cold 5 percent formalin in PBS. After washing twice with PBS, the organisms were suspended in a 0.05 mg/ml solution of the labeled antibody in PBS and incubated for 45 minutes at 37° C. Mounting and photography were as described above.

Immunoaffinity Purification

Purified immunoglobulins were dialyzed against 1 liter of 0.1 M NaHCO$_3$ buffer, pH 8.0, prior to coupling to Affi-Gel 10: N-hydroxysuccinimide ester of agarose (Bio-Rad Laboratories, Richmond, CA.). A ratio of 0.5 mg immunoglobulins per ml beads were used and the reaction was carried out at 4° C. for 5 hours. Unreacted sites were then blocked by addition of 0.1 ml of 1 M ethanolamine HCl, pH 8.0, per ml beads for 2 hours at 4° C. A 0.5 ml column of antibody-Affi-Gel 10 beads was washed with 10 ml of column buffer (50 mM Tris-HCl, pH 7.6, 100 mM NaCl and 0.2 percent Triton X-100), followed by washing with 5 ml of elution buffer (2 M KSCN in column buffer), and finally 20 ml of column buffer. Male worm glycoproteins isolated and iodinated as described above were applied to the column. The column was washed with column buffer until the counts eluted were at background level. The proteins bound to the immunoglobulin were then recovered with elution buffer.

EXAMPLE 1

Cercarial glycoproteins purified by lectin-affinity chromatography were labeled with $^{125}$Iodine and analyzed by SDS-polyacrylamide gel electrophoresis. There were 15 major polypeptides ranging in mass from 190 kilodaltons to 9 kilodaltons. Sera of infected humans or mice precipitated all of these glycoproteins. No precipitation was observed with normal human or mouse serum. Although the pattern of immunoprecipitated proteins was similar with sera from individual humans, there were distinctive differences between some of these sera.

The immune response of the mice immunized with purified cercarial glycoproteins was compared to that of the infected humans. Hyperimmune mouse serum, withdrawn after 7 injections over a period of 11 weeks, gave an immunoprecipitation pattern very similar to that observed with serum of an infected human, as analyzed by two-dimensional gel electrophoresis. The autoradiograms were overexposed in order to visualize minor polypeptides. Glycoproteins analyzed by this gel technique frequently show multiple spots or isomorphs due to charge differences caused by carbohydrate heterogeneity. This analysis showed most importantly that the immune response in humans was equally as strong as that elicited by hyperimmunized mice.

Two 8 week old C57BL/6 mice were immunized intraperitoneally with 70 ug purified cercarial glycoproteins per injection. The spleen cells were fused with X63-Ag8-653 myeloma cells. The procedures employed are described above. The screening was for monoclonal antibodies that precipitate the same glycoproteins as do sera from infected humans. Three fused cell hybrids of this invention, ATCC HB-8086; ATCC HB-8087 and ATCC HB-8088, were obtained.

EXAMPLE 2

The reactivity of the antibodies produced by hybridoma ATCC HB-8087 were tested by analysis of immunoprecipitates of $^{125}$I-labeled cercarial glycoproteins. Two polypeptides with apparent molecular weights of 35,000 and 20,000 were precipitated by this monoclonal antibody. These same two polypeptides were also present when analogous immunoprecipitates were analyzed on SDS-polyacrylamide gel without reduction, thus excluding their coprecipitation by disulfide bonding. Preliminary results from two-dimensional tryptic peptide mapping showed the presence of shared peptides, indicating the 35,000 and 20,000 dalton polypeptides were derived by proteolytic cleavage.

The serum of an infected human and the monoclonal antibody both precipitated glycoproteins with the same apparent molecular weight. These immunoprecipitates were therefore further analyzed by two-dimensional gel electrophoresis to ascertain whether these were the same protein. The monoclonal antibody precipitated 14 isomorphs, pH 6.3-5.3, with molecular weights ranging from 32,000 to 35,000 and 2 isomorphs, pH 5.3-4.8 at 20,000 daltons. Each of these isomorphs were superimposable with polypeptides immunoprecipitated with serum of an infected human. Two-dimensional analysis of immunoprecipitates obtained with additional sera of different patients infected with schistosomiasis gave the same results. Sera of uninfected humans or mice were negative. Therefore, the monoclonal antibody produced by hybridoma ATCC HB-8087 identified a glycoprotein, expressed in cercariae, which elicits an immune response in infected humans.

EXAMPLE 3

Immunoprecipitates of adult female and male worms were analyzed to establish that the antigenic determinant of cercarial proteins recognized by antibodies of ATCC HB-8087 was expressed in other developmental stages and to identify the protein molecules expressing these antigenic determinants The $^{125}$I-labeled glycoproteins of adult worms, isolated as described above, were immunoprecipitated with ATCC HB-8087 monoclonal antibody, with serum of an infected human, as well as the anti-cercarial glycoprotein serum. The immunoprecipitates were analyzed by SDS-polyacrylamide gel electrophoresis. Infected human serum precipitated over 15 glycoproteins of the female worms that were visualized as present in high concentration or intensely labeled. The pattern of glycoproteins immunoprecipitated from male worms was markedly different; 9 glycoproteins present in high concentration or intensely labeled were visualized. It appears that the differences in immunoreactivity between male and female worms may be due to the presence of egg glycoproteins in the female worm extract, since eggs would be contained in the female worms when they were isolated from the mice. A protein of 170 kilodaltons was immunoprecipitated from both male and female worms by serum of infected humans and served as a marker for comparing the immunoprecipitated proteins.

ATCC HB-8087 monoclonal antibody also precipitated proteins from both male and female worms. A 200 kilodalton protein was precipitated from the male worm extract, along with a minor component of 43 kilodaltons that was visible upon longer exposure of a radioautograph. The proportions of these two immunoprecipitated glycoproteins was variable, depending on the age of the worm extract. A second immunoprecipitation carried out 6 days later with the same $^{125}$I-labeled male worm preparation showed that 60 percent of the precipitate was at 200 kilodaltons and 40 percent of the precipitate was at 43 kilodaltons. All the other proteins immunoprecipitated by the polyclonal sera showed no change, indicating that the glycoprotein recognized by ATCC HB-8087 antibodies was susceptible to proteolytic fragmentation even in the presence of PMSF.

The antigenic targets of the male and female worm recognized by ATCC HB-8087 monoclonal antibody were different. A 43 kilodalton polypeptide was also immunoprecipitated from the female worm, but in contrast to the 200 kilodalton male polypeptide, the female worm showed immunoprecipitation of proteins at 160 kilodaltons and 155 kilodaltons. At least one of the proteins is possibly an egg form, since this monoclonal antibody recognized antigenic determinants present in an egg extract, as measured by direct binding.

The pattern of proteins of male or female worms immunoprecipitated with serum of an infected human showed extensive similarity to that obtained with serum of mice immunized with cercarial glycoproteins.

The relationship between the $^{125}$I-labeled male worm glycoproteins precipitated with the monoclonal antibody or the infected human serum were also analyzed by two-dimensional gel electrophoresis. Immunoprecipitates with ATCC HB-8087 monoclonal antibody contained 13 isomorphs which were superimposable wih those of infected human, showing that the protein recognized had the same charge (pI) and molecular weight. These results indicate that the proteins are the same.

EXAMPLE 4

The specificity of binding of ATCC HB-8087 monoclonal antibody was measured by direct binding assays. Increasing amounts of male worm extract were coated to a plastic surface which has been pretreated with poly-L-lysine and the amount of $^{125}$I-labeled purified ATCC HB-8087 monoclonal antibody immunoglobulin bound was measured. The results are shown in FIG. 1. The antibody binding demonstrated antigen concentration dependence. The binding was specific, as other nonrelevant monoclonal antibodies did not bind the schistosomal proteins, even at high antigen concentrations.

The relative concentration of antigen recognized by ATCC HB-8087 monoclonal antibody in different developmental stages of the schistosome was measured by direct binding assays. Equal amounts of schistosomal proteins extracted from eggs, female worms, male worms or cercariae were coated to a plastic surface as described above and the amount of $^{125}$I-labeled purified ATCC HB-8087 monoclonal antibody immunoglobulin bound was measured. The results are shown in FIG. 2 and demonstrate that the antigen was expressed in each of the developmental stages. The concentration of this antigen appeared to be highest in the male worm with approximately 3 fold less in each of the other extracts. Cercarial extracts solubilized sequentially by different agents as described above showed the same specific activity for this antigen, in contrast to that observed with other antigens. The results also showed that the binding of the ATCC HB-8087 monoclonal antibody was specific and the antigenic sites were saturable.

EXAMPLE 5

Figure 3:
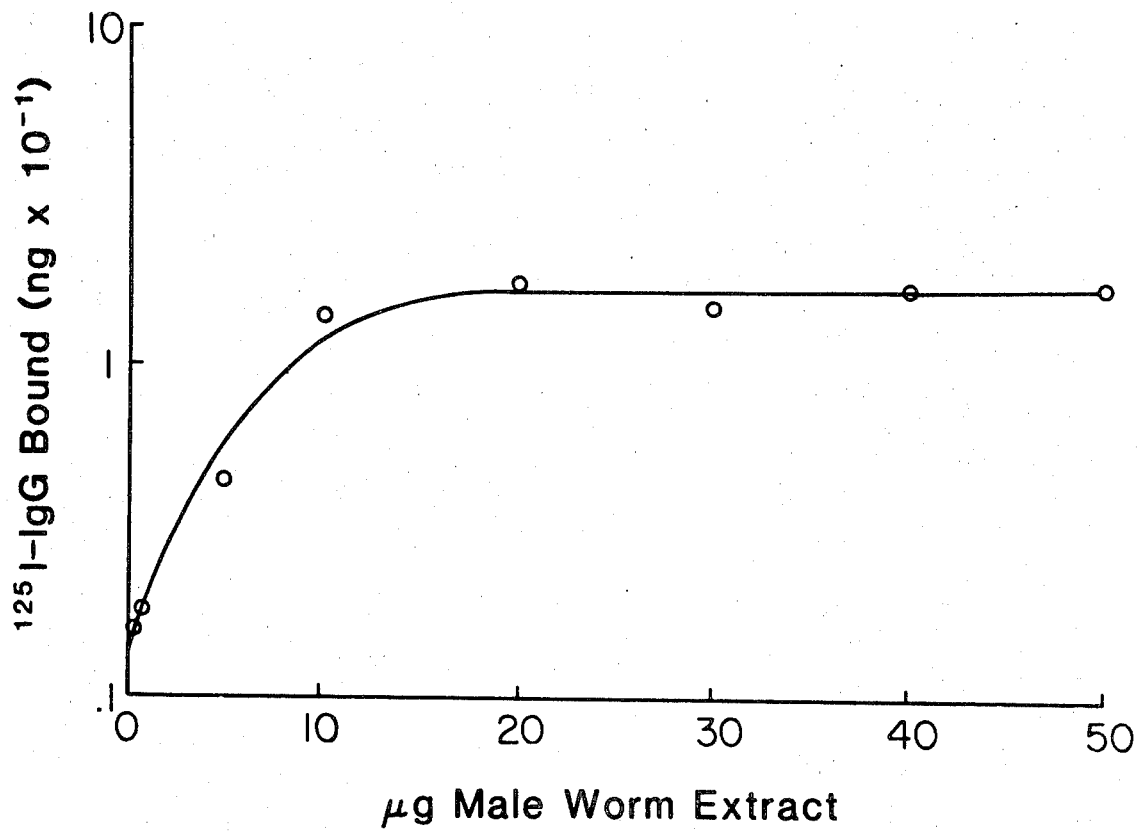

The specificity of binding of ATCC HB-8088 monoclonal antibody was measured by direct binding assay. The amount of $^{125}$I-labeled purified immunoglobulin bound to increasing amounts of male worm extract coated to polystyrene microtiter wells was measured and is shown in FIG. 3. The nonspecific binding of 100 ng of $^{125}$I-labeled P3 was subtracted from the binding obtained with 100 ng of $^{125}$I-labeled test antibody for FIG. 3. The antibody binding showed antigen concentration dependence and was saturable.

Figure 4:
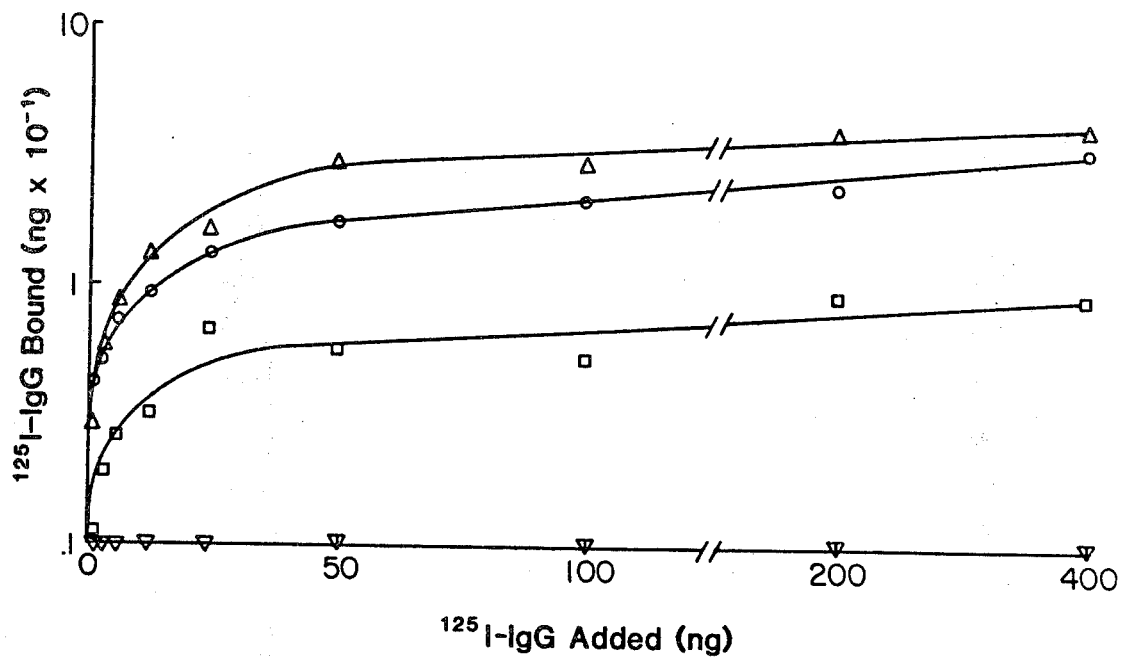

The relative concentration of antigen recognized by the monoclonal antibody in different schistosome developmental stages was measured by direct binding as described above. In this case, equal amounts of schistosomal protein extracts were used and the results are depicted in FIG. 4. The nonspecific binding of equivalent amounts of $^{125}$I-labeled P3 was subtracted for FIG. 4. The antigen was expressed in cercariae and adult worms, both male and female, but was not detected in egg protein extract. Each of the cercarial extracts solubilized sequentially by different agents as described above were assayed for binding by the monoclonal antibody. The highest specific activity for this antigen was observed with the Triton X-305 solubilized extract which is consistent with an antigen that is an integral membrane component. The concentration of this antigen was three-fold higher in cercariae and male worms that in female worms.

EXAMPLE 6

The antigenic target of the ATCC HB-8088 monoclonal antibody was identified by immunoprecipitation of $^{125}$I-labeled cercarial glycoproteins. A polypeptide with an apparent molecular weight of 120,000 was precipitated. Normal mouse serum or nonrelevant monoclonal antibody of the same immunoglobulin class (IgG$_1$) showed no precipitation.

Analogous immunoprecipitations were also carried out with $^{125}$I-labeled glycoproteins of either male or female worms. In both of these cases the monoclonal antibody precipitated a polypeptide of 170,000 daltons.

EXAMPLE 7

The serum of an infected human and the ATCC HB-8088 monoclonal antibody both precipitated a cercarial glycoprotein with the same apparent molecular weight. These immunoprecipitates were therefore further analyzed by two-dimensional gel electrophoresis to ascertain whether these were indeed the same protein. The monoclonal antibody precipitated 7 isomorphs, pH 7.1-6.8, with molecular weights of 120,000. Each of these isomorphs were superimposable with those immunoprecipitated with infected human serum. Sera of additional patients infected with schistosomiasis gave the same results. Sera of uninfected humans or mice were negative.

The homology of $^{125}$I-labeled cercarial glycoprotein immunoprecipitated with the monoclonal antibody or sera of two different infected humans was also analyzed by two-dimensional tryptic peptide mapping. The three tryptic peptide maps were indistinguishable. Thus, the monoclonal antibody identified a glycoprotein which elicits an immune response in infected humans.

EXAMPLE 8

The anatomic location of the antigen recognized by ATCC HB-8088 monoclonal antibody was analyzed by indirect immunofluorescent microscopy. Artificially transformed schistosomula were examined because they represent a reproducibly prepared form of the larval stage which is the first to be contracted by the immune system of the vertebrate host (Brink et al., Parasitology, 74, 73-86 (1977)).

Schistosomula were prepared essentially as described by Ramalho-Pinto et al, Exp. Parasitology, 36, 360-372 (1974). Aliquots of 2 to 3 ml of the cercarial suspension in aquarium water were measured into 15 ml Falcon tubes so that each tube contained about 1500 organisms. The cercariae were chilled on ice for 10 min., centrifuged for 2 min. at 800 rpm in a table-top centrifuge, washed in HBSS, centrifuged again, and suspended in 0.5 ml heat-inactivated normal mouse serum containing 100 units/ml penicillin, 100 μg/ml steptomycin, and 0.025 μg/ml Fungizone ® (Gibco). The suspensions were vortexed for 2 min., then incubated for 3 hours at 37° C. Viability of the organisms was checked microscopically, and after addition of PMSF to a final 2 mM concentration, the schistosomula were washed in PBS. Fixed preparations were obtained by suspending the organisms in 10 ml of 5 percent formalin in PBS for 20 min., then washing twice with 10 ml PBS. Between washes, the schistosomula were pelleted for 2 min. at 800 rpm in a table-top centrifuge.

Schistosoumula, both fixed and unfixed, were examined with normal mouse serum and purified myeloma P3 immunoglobulin. Surface deposition of fluorescent label was limited to the points of attachment that had existed between the schistosomula body and the cercarial tail. The strong fluorescence at this location was occasionally observed with all antisera.

Serum of hyperimmune mice stained the entire schistosomular surface. Under oil immersion, the parasite's surface appeared uniformly bright, and punctuated by what appeared to be numerous pores. The patterns of fluorescence obtained were the same with both fixed and unfixed specimens.

The fluorescence pattern obtained with ATCC HB-8088 monoclonal antibody, was restricted to the spines of the organism. These structures were present over the entire surface, but were brightest and most clearly defined at the poles, which were covered with 20 to 25 rows of short spines. After aldehyde fixation, the spines were more distinct and appeared to be about one micrometer in length, and, at the anterior end of the organism, to be oriented in an antero-posterior direction.

Directly stained schistosomula exhibited a pattern identical to that of indirectly stained schistosomula. No deposition of rhodamine conjugated control immunoglobulin was detected on the schistosomular surface.

EXAMPLE 9

The distribution of the antigenic target recognized by ATCC HB-8088 antibody on the tegument of adult worms was studied by direct immunofluorescence because extensive amounts of murine immunoglobulin on the parasite's surface precluded use of the indirect technique. Surface deposition of the negative control P3 immunoglobulin was not detected, while male worms were extensively stained by ATCC HB-8088 antibody. The spines attached to the tubercles on the dorsum of the worm were brightly illuminated and a few scattered spines were observed elsewhere. On female worms, spines were present mainly over the posterior surface and were similar to appearance to those concentrated on the male tubercles.

EXAMPLE 10

Immunoaffinity chromatography permitted a simple one-step purification of the spine glycoprotein. A single band with an indicated molecular weight of 170,000 was observed following elution of the column with the chaotropic reagent, KSCN. The yield appeared to be maximal, since this glycoprotein was not visible in the column runthrough, whereas it was clearly seen in the glycoprotein mixture which was applied to the column.

EXAMPLE 11

The anatomic location of the antigens recognized by ATCC HB-8086 monoclonal antibody was analyzed by indirect immunofluorescent microscopy. Artificially transformed schistosomula were examined because they represent a reproducibly prepared form of the larval stage which is the first to be contacted by the immune system of the vertebrate host.

The antigen recognized by ATCC HB-8086 monoclonal antibody was seen as a striking pattern of a very large number of narrow bands, punctuated by brighter regions suggesting cross-bridges, and running horizontally around the entire schistosomulum.

The distribution of the antigenic targets recognized by ATCC HB-8086 antibody on the tegument of adult worms was studied by direct immunofluorescence because extensive amounts of murine immunoglobulin on the parasite's surface precluded use of the indirect technique. Surface deposition of the negative control P3 immunoglobulin was not detected. ATCC HB-8086 monoclonal antibody exhibited a fluorescence pattern on adult worms, which was remarkably similar to that observed on schistosomula. Once again, a very large number of widely distributed narrow bands were observed. In addition, the tubercles on the dorsum of the male worm were illuminated, demonstrating that this molecule was common to the tubercles, as well. Directly stained schistosomula exhibited a pattern identical to that of indirectly stained schistosomula. No deposition of rhodamine conjugated control immunoglobulin was detected on the schistosomular surface. These results demonstrate that this antibody identifies an antigenic site which occurs with great frequency in the membrane. This site, therefore, is an advantageous site for a immunoprophylaxis.

Although the above examples utilized *S. mansoni,* other flukes provide comparable results. Indeed, the monoclonal antibodies described above can be useful with species other than *S. mansoni.*

Since modifications of this invention will be apparent to those skilled in the art, it is intended that the invention be limited only by the scope of the appended claims.

I claim:

1. A screening method for the determination of a fluke infection of a warm-blooded animal which comprises testing a body component selected from the group consisting of serum, urine, milk and feces for the presence of glycoprotein molecules bound by antibodies produced by fused cell hybrid ATCC HB-8087 or fused cell hybrid ATCC HB-8086.

2. The method of claim 1 wherein the body component is urine.

3. The method of claim 1 wherein the body component is feces.

4. The method of claim 1 wherein said glycoprotein molecules are identified by an antibody assay selected from the group consisting of immunofluorescence, radioimmunoassay, and enzyme assay.

5. The method of claim 1 wherein said warm-blooded animal is a human.

6. A screening method for the determination of a fluke infection in a warm-blooded animal which comprises testing body serum for the presence of antibodies which bind glycoprotein molecules that are bound by the antibodies produced by fused cell hybrid ATCC HB-8087 or fused cell hybrid ATCC HB-8086.

7. The method of claim 6 wherein a human is tested.

8. A method of combating fluke infection which comprises injecting a warm-blooded animal with a mixture of antibodies corresponding to the antibodies produced by fused cell hybrids ATCC HB-8086, ATCC HB-8087 and ATCC HB-8088.

9. A method of combating fluke infection which comprises injecting a warm-blooded animal with a mixture of purified protein molecules bound by antibodies produced by fused cell hybrids ATCC HB-8086, ATCC HB-8087 and ATCC HB-8088.

* * * * *